United States Patent [19]

Izumi et al.

[11] Patent Number: 4,755,214
[45] Date of Patent: Jul. 5, 1988

[54] COMPOSITION FOR REGULATING PLANT GROWTH

[75] Inventors: Kazuo Izumi, Takarazuka; Hiromichi Oshio, Osaka, both of Japan

[73] Assignee: Sumitomo Chemical Company, Limited, Osaka, Japan

[21] Appl. No.: 798,349

[22] Filed: Nov. 15, 1985

Related U.S. Application Data

[63] Continuation of Ser. No. 604,597, Apr. 27, 1984, abandoned.

[30] Foreign Application Priority Data

May 6, 1983 [JP] Japan .................................. 58-79874
May 6, 1983 [JP] Japan .................................. 58-79875

[51] Int. Cl.⁴ .......................................... A01N 43/64
[52] U.S. Cl. .......................................... 71/92
[58] Field of Search ............................... 71/92

[56] References Cited

FOREIGN PATENT DOCUMENTS 0054431  6/1982  European Pat. Off. .
3045182  7/1982  Fed. Rep. of Germany .
2004276  3/1979  United Kingdom .
2046260 11/1980  United Kingdom .

OTHER PUBLICATIONS

Research Disclosure, No. 176 (1978), pp. 44-47.
Worthing, The Pesticide Manual, 6th Edition, p. 145, (1979).

Primary Examiner—Catherine L. Mills
Attorney, Agent, or Firm—Stevens, Davis, Miller & Mosher

[57] ABSTRACT

A composition for regulating the growth of plants which comprises as active ingredients an effective amount of (E)-1-(4-chlorophenyl)-4,4-dimethyl-2-(1,2,4-triazol-1-yl)-1-pentene-3-ol and one or more compounds selected from the group consisting of 2-chloro-4,6-bis(ethylamino)-s-triazine, 2-chloro-4-ethylamino-6-isopropylamino-s-triazine and a phenoxyacetic acid type compound represented by the formula,

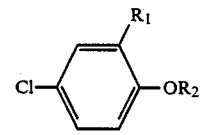

wherein $R_1$ represents a chlorine atom or methyl group, and $R_2$ represents a carboxymethyl, carboxyethyl or carboxypropyl group, and an inert carrier.

8 Claims, No Drawings

COMPOSITION FOR REGULATING PLANT GROWTH

This application is a continuation of application Ser. No. 604,597, filed Apr. 27, 1984 now abandoned.

The present invention relates to a composition for regulating the growth of plants which comprises as active ingredients (E)-1-(4-chlorophenyl)-4,4-dimetyl-2-(1,2,4-triazol-1-yl)-1-pentene-3-ol (hereinafter referred to as compound A) and one or more compounds selected from the group consisting of 2-chloro-4,6-bis(ethylamino)-s-triazine (hereinafter referred to as simazine), 2-chloro-4-ethylamino-6-isopropylamino-s-triazine (hereinafter referred to as atrazine) and a phenoxyacetic acid type compound represented by the formula (I),

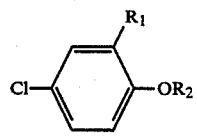

wherein $R_1$ represents a chlorine atom or methyl group, and $R_2$ represents a carboxymethyl, carboxyethyl or carboxypropyl group, and an inert carrier.

Hitherto, many herbicides are used for controlling weeds in non-cultivation lands, turf lands and the like.

In non-cultivation lands, however, the kind of weeds to be controlled is so diversified and the duration of their generation is so long that weed controlling agents having both a strong weed controlling activity and a wide weed controlling spectrum are desired. Further, as to weeds growing at the sides of a road and railway track, their complete extermination increases a danger of the soil being degraded by rainfall, etc. so that it is desired to control the weeds so as to simultaneously achieve both partial extermination of the weeds and the growth retardation of the remaining weeds. Also, for weed controlling agents used in turf lands, it is desired that they do not inhibit the growth of lawn grass and therefore give no phytotoxicity to the grass, while that they can selectively exterminate or control weeds in the turf lands.

The present inventors extensively studied on plant growth regulating agents satisfying these objects, and as a result, found that the compositions of the present invention have a moderate control over weeds in non-cultivation lands and besides give no such phytotoxicity as to become a problem to lawn grass.

That the compound A can be used as an active ingredient for plant growth regulating agents or herbicides is described in GB Pat. No. 2046260B. Also, that simazine and atrazine can be used as an active ingredient for herbicides is described in C. R. Worthing: The Pesticide Manual, 6th ed., pp 22 & 474, 1979. Further, that some of the phenoxyacetic acid type compounds represented by the formula (I) can be used as an active ingredient for herbicides is described in C. R. Worthing: The Pesticide Manual, 6th ed., pp 145, 149, 179, 326, 327, 329, etc., 1979. Some of the compounds will be shown in Table 1. These phenoxyacetic acid type compounds include, in addition to the carboxylic acid, the salts of the acid and esters thereof with a lower alcohol.

TABLE 1

Phenoxyacetic acid type compounds represented by the formula,

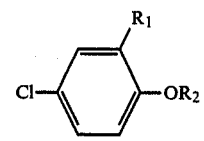

| $R_1$ | $R_2$ | General name |
|---|---|---|
| Cl | —$CH_2CO_2H$ | 2,4-D |
| Cl | —$(CH_2)_3CO_2H$ | 2,4-DB |
| Cl | —$CHCO_2H$ with $CH_3$ | Dichlorprop |
| $CH_3$ | —$CH_2CO_2H$ | MCPA |
| $CH_3$ | —$(CH_2)_3CO_2H$ | MCPB |
| $CH_3$ | —$CHCO_2H$ with $CH_3$ | Mecoprop |

The compositions of the present invention have an exterminating or growth retarding activity on weeds in question in non-cultivation lands and turf lands, but give no such phytotoxicity as to become a problem to lawn grass. Said weeds in question include for example dicotyledonous weeds such as hairy fleabane (*Erigeron bonariensis*), horseweed (*Erigeron canadensis*), hairy galinsoga (*Galinsoga ciliata*), common groundsel (*Senecio vulgaris*), annual sowthistle (*Sonchus oleraceus*), annual fleabane (*Erigeron annuus*), mugwort (*Artemisia vulgaris*), ladysthumb (*Polygonum persicaria*), common vetch (*Vicia sativa*), kudzu (*Pueraria lobata* Ohwi), white clover (*Trifolium repens*), woodsorrel sp. (*Oxalis corniculata*), lawn pennywort (*Hydrocotyle sibthorpioides*), henbit (*Lamium amplexicaure*), birdseye speedwell (*Veronica persica*), etc., and monocotyledonous weeds such as green foxtail (*Seteria viridis*), large crabgrass (*Digitaria sanguinalis*), goose grass (*Eleusine indica*), Johnsongrass (*Sorghum halepense*), purple nutsedge (*Cyperus rotundus*), etc.

When the compositions of the present invention are used in non-cultivation lands and turf lands, they are generally formulated into preparation forms such as emulsifiable concentrates, wettable powders, suspension concentrates and the like by mixing with an inert carrier such as solid or liquid carrier, surface active agent and other auxiliaries. These compositions contain as active ingredients the compound A and one or more compounds selected from simazine, atrazine and the phenoxyacetic acid type compound represented by the formula (I) in a rate of 1 to 95 wt.%, preferably 5 to 80 wt.%, and the mixing weight ratio of the compound A to the other compounds of the active ingredient is 1 to 0.5-200, preferably 1 to 1-80.

The solid carrier includes for example fine powders or granules of kaolin clay, attapulgite clay, bentonite, fuller's earth, pyrophyllite, talc, diatomaceous earth, calcite, walnut powder, urea, ammonium sulfate, synthetic hydrated silicon dioxide and the like. The liquid carrier includes for example hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton seed oil), dimethyl sulfoxide, acetonitrile, water and the like.

The surface active agent used for emulsification, dispersion, wetting, etc. includes for example anionic surface active agents such as salts of alkyl sulfate, alkyl(aryl)sulfonates, dialkyl sulfosuccinates, salts of polyoxyethylene alkylaryl ether phosphoric acid ester, etc., and nonionic ones such as polyoxyethylene alkyl ether, polyoxyethylene polyoxypropylene block copolymers, sorbitan fatty acid esters, polyoxyethylene sorbitan fatty acid esters, etc. The auxiliaries for formulation include for example lignosulfonates, alginates, polyvinyl alcohol, gum arabic, CMC (carboxymethyl cellulose), PAP (isopropyl acid phosphate) and the like.

Preparation examples for the composition of the present invention will be shown. In the examples, all parts are by weight.

PREPARATION EXAMPLE 1

10 Parts of the compound A, 10 parts of simazine or 2,4-D, 3 parts of calcium lignosulfonate, 2 parts of sodium lauryl sulfate and 75 parts of synthetic hydrated silicon dioxide are thoroughly pulverized and mixed together to obtain a wettable powder.

PREPARATION EXAMPLE 2

5 Parts of the compound A, 10 parts of atrazine or MCPA, 14 parts of polyoxyethylene styrylphenyl ether, 6 parts of calcium dodecylbenzenesulfonate and 65 parts of xylene are thoroughly mixed together to obtain an emulsifiable concentrate.

PREPARATION EXAMPLE 3

10 Parts of the compound A, 10 parts of simazine or 2,4-D, 3 parts of polyoxyethylene sorbitan monooleate, 3 parts of CMC and 74 parts of water are mixed and wet-pulverized until the particle size is reduced to not more than 5μ to obtain a suspension concentrate.

PREPARATION EXAMPLE 4

5 Parts of the compound A, 10 parts of atrazine or the sodium salt of 2,4-D, 1 part of polyoxyethylene styrylphenyl ether and 84 parts of water are mixed to obtain a liquid formulation.

PREPARATION EXAMPLE 5

10 Parts of the compound A, 5 parts of 2,4-D, 5 parts of dichlorprop, 3 parts of calcium lignosulfonate, 2 parts of sodium lauryl sulfate and 75 parts of synthetic hydrated silicon dioxide are thoroughly pulverized and mixed together to obtain a wettable powder.

PREPARATION EXAMPLE 6

5 Parts of the compound A, 20 parts of atrazine, 20 parts of simazine, 3 parts of calcium lignosulfonate, 2 parts of sodium lauryl sulfate and 50 parts of synthetic hydrated silicon dioxide are thoroughly pulverized and mixed together to obtain a wettable powder.

PREPARATION EXAMPLE 7

5 Parts of the compound A, 10 parts of atrazine or simazine, 10 parts of 2,4-D, 3 parts of calcium lignosulfonate, 2 parts of sodium lauryl sulfate and 70 parts of synthetic hydrated silicon dioxide are thoroughly pulverized and mixed together to obtain a wettable powder.

These compositions, either as such or in dilution with water, can be applied to pastures, uplands, orchards, forests and the like in addition to non-cultivation lands and turf lands wherein weeds are generated or considered to be generated. The dosage rate is 0.1 to 200 g, preferably 1 to 100 g, as the amount of active ingredient, per are. When they are used in dilution with water, the dosage rate is 1 to 100 liters per are. This dosage rate may properly be changed depending upon weather conditions, the kind of preparations, application times, application methods, application sites, the kind of intended weeds and the like.

The growth retarding activity of the compositions of the present invention will be illustrated with reference to the following examples. Hereupon, the growth retarding activity was obtained as follows: The test plants on examination are visually observed for a degree of germination and a degree to which their growth has been inhibited; and these degrees are expressed by indices, 0, 1, 2, 3, 4 and 5, wherein 0 means that there is little or no difference between the treated and untreated plots, 5 means that the plants have been exterminated or their growth has been completely inhibited, and wherein the indices 1, 2, 3 and 4 mean four grades between 0 and 5.

EXAMPLE 1

Before germination of weeds in spring, the ground at the side of a road was divided into plots of 3 m×3 m each. At that point, the prescribed amount of each of the wettable powders, as produced from the test compounds in Table 2 according to Preparation Example 1, was diluted with water corresponding to 10 liters per are, and sprayed onto the above plot by means of a hand sprayer. The growth retarding activity was examined three months after the spraying. The test was carried out using two plots per treatment, and the average results obtained were shown in Table 2.

TABLE 2

| Test Compound | Dosage rate of active ingredient (g/a) | Growth retarding activity | | | |
|---|---|---|---|---|---|
| | | Ladysthumb | Annual fleabane | Hairy fleabane | Green foxtail |
| Compound A | 10 | 4 | 3 | 3 | 4 |
| | 5 | 3 | 2 | 2 | 4 |
| Simazine | 10 | 3 | 2 | 1 | 3 |
| | 5 | 2 | 1 | 0 | 2 |
| Atrazine | 10 | 3 | 2 | 1 | 3 |
| | 5 | 2 | 1 | 0 | 2 |
| 2,4-D | 20 | 2 | 2 | 1 | 0 |
| | 10 | 1 | 1 | 0 | 0 |
| Sodium salt of 2,4-D | 20 | 2 | 2 | 1 | 0 |
| | 10 | 1 | 1 | 0 | 0 |
| Compound A + simazine | 10 + 5 | 5 | 4 | 4 | 5 |
| Compound A + atrazine | 10 + 5 | 5 | 4 | 4 | 5 |

TABLE 2-continued

| Test Compound | Dosage rate of active ingredient (g/a) | Growth retarding activity | | | |
|---|---|---|---|---|---|
| | | Ladysthumb | Annual fleabane | Hairy fleabane | Green foxtail |
| Compound A + 2,4-D | 10 + 10 | 5 | 4 | 4 | 4 |
| Compound A + sodium salt of 2,4-D | 10 + 10 | 5 | 4 | 4 | 4 |
| No treatment | — | 0 | 0 | 0 | 0 |

EXAMPLE 2

A turf land of Korai lawn grass which had elapsed five years after creation was divided into plots of 3 m×3 m each. At the first third of March before the germination of lawn grass, the prescribed amount of each of the wettable powders, as produced from the test compounds in Table 3 according to Preparation Example 1, was diluted with water corresponding to 10 liters per are, and sprayed onto the above plot by means of a hand sprayer. At the first third of June three months after the spraying, the growth retarding activity was examined. The test was carried out using two plots per treatment, and the average results obtained were shown in Table 3.

TABLE 3

| Test compound | Dosage rate of active ingredient (g/a) | Growth of retarding activity | | | | Phytotoxicity to Korai lawn grass |
|---|---|---|---|---|---|---|
| | | Lawn pennywort | Woodsorrel sp. | Birdseye speedwell | Large crabgrass | |
| Compound A | 5 | 4 | 4 | 4 | 4 | 0 |
| | 2.5 | 3 | 3 | 4 | 3 | 0 |
| Simazine | 10 | 1 | 2 | 3 | 3 | 0 |
| | 5 | 0 | 1 | 2 | 2 | 0 |
| Atrazine | 10 | 2 | 2 | 3 | 3 | 0 |
| | 5 | 0 | 1 | 2 | 2 | 0 |
| 2,4-D | 20 | 2 | 0 | 3 | 0 | 0 |
| | 10 | 1 | 0 | 2 | 0 | 0 |
| MCPA | 20 | 1 | 0 | 3 | 0 | 0 |
| | 10 | 1 | 0 | 2 | 0 | 0 |
| Compound A + simazine | 2.5 + 5 | 5 | 4 | 5 | 5 | 0 |
| Compound A + atrazine | 2.5 + 5 | 5 | 4 | 5 | 5 | 0 |
| Compound A + 2,4-D | 2.5 + 20 | 5 | 4 | 5 | 4 | 0 |
| | 2.5 + 10 | 4 | 4 | 5 | 4 | 0 |
| Compound A + MCPA | 2.5 + 20 | 5 | 4 | 5 | 4 | 0 |
| | 2.5 + 10 | 4 | 4 | 5 | 4 | 0 |
| No treatment | — | 0 | 0 | 0 | 0 | 0 |

What is claimed is:

1. A composition for retarding the growth of plants which comprises as active ingredients an effective amount of (E)-1-(4-chlorophenyl)-4,4-dimethyl-2-(1,2,4,-triazol-1-yl)-1-pentene-3-ol and one or more compounds selected from the group consisting of 2-chloro-4,6-bis-(ethylamino)-s-triazine, 2-chloro-4-ethylamino-6-isopropylamino-s-triazine and a phenoxyacetic acid type compound represented by the formula,

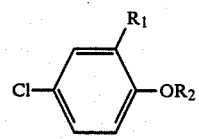

wherein $R_1$ represents a chlorine atom or methyl group, and $R_2$ represents a carboxymethyl, carboxyethyl or carboxypropyl group, in an amount of 1 to 8 parts by weight based on 1 part of weight of (E)-1-(4-chlorophenyl)-4,4,-dimethyl-2-(1,2,4-triazol-1-yl)-1-pentene-3-ol, and an inert carrier.

2. The composition according to claim 1 containing as active ingredients (E)-1-(4-chlorophenyl)-4,4-dimethyl-2-(1,2,4-triazol-1-yl)-1-pentene-3-ol and 2-chloro-4,6-bis(ethylamino)-s-triazine.

3. The composition according to claim 1 containing as active ingredients (E)-1-(4-chlorophenyl)-4,4-dimethyl-2-(1,2,4-triazol-1-yl)-1-pentene-3-ol and 2-chloro-4-ethylamino-6-isopropylamino-s-triazine.

4. The composition according to claim 1 containing as active ingredients (E)-1-(4-chlorophenyl)-4,4-dimethyl-2-(1,2,4-triazol-1-yl)-1-pentene-3-ol and 2,4-dichlorophenoxyacetic acid.

5. The composition according to claim 1 containing as active ingredients (E)-1-(4-chlorophenyl)-4,4-dimethyl-2-(1,2,4-triazol-1-yl)-1-pentene-3-ol and sodium 2,4-dichlorophenoxyacetate.

6. The composition according to claim 1 containing as active ingredients (E)-1-(4-chlorophenyl)-4,4-dimethyl-2-(1,2,4-triazol-1-yl)-1-pentene-3-ol and 4-chloro-o-tolyloxyacetic acid.

7. A method for regulating the growth of plants which comprises applying a regulatorily effective amount of the composition according to claim 1, to the plants.

8. The composition according to claim 1 wherein the phenoxyacetic acid type compound is present in the form of its salt or as an ester with a lower alcohol.

* * * * *